United States Patent [19]

Lloyd et al.

[11] Patent Number: 4,678,747

[45] Date of Patent: Jul. 7, 1987

[54] MONOCLONAL ANTIBODIES FOR DETECTION OF AN H (O) BLOOD GROUP ANTIGEN

[75] Inventors: Kenneth O. Lloyd, Bronx; Lloyd J. Old, New York, both of N.Y.; Karl-Anders Karlsson, Gothenburg, Sweden; Goran Larson, Gothenburg, Sweden; Nicklas Stromberg, Gothenburg, Sweden; Jan Thurin, Gothenburg, Sweden; Bernd R. Anger, Kreiensen, Fed. Rep. of Germany; Herbert F. Oettgen, New Canaan, Conn.

[73] Assignee: Sloan-Kettering Institute, New York, N.Y.

[21] Appl. No.: 470,815

[22] Filed: Feb. 28, 1983

Related U.S. Application Data

[63] Continuation of Ser. No. 467,999, Feb. 18, 1983, abandoned.

[51] Int. Cl.[4] .................. G01N 53/00; C12N 15/00
[52] U.S. Cl. .............................. 435/7; 424/85; 435/68; 435/172.2; 435/240; 435/241; 435/940; 436/548; 530/387; 935/95; 935/110; 935/96

[58] Field of Search ............... 435/68, 172.2, 7, 240, 435/948; 530/387; 424/85; 436/548; 935/95, 110

[56] References Cited

U.S. PATENT DOCUMENTS 4,443,427  4/1984  Reinherz .......................... 435/68

OTHER PUBLICATIONS

Hybridoma–vol. 1, No. 2, (1982), pp. 169–225.
Anger et al.–Hybridoma–vol. 1, No. 2 (1982), pp. 139–147.
Knowles et al.–J. of Immunogenics vol. 9 (1982) pp. 69–76.

*Primary Examiner*—Sam Rosen
*Attorney, Agent, or Firm*—John P. White

[57] ABSTRACT

Monoclonal antibodies recognizing the difucosyl-type-2-H antigen on human cells and a method of producing said antibodies are disclosed. The monoclonal antibodies are useful in blood typing and in diagnosis of blood disorders and malignancies involving loss or gain of this H antigen.

14 Claims, No Drawings

MONOCLONAL ANTIBODIES FOR DETECTION OF AN H (O) BLOOD GROUP ANTIGEN

This present invention was wholly or partially made with funds provided by the Department of Health and Human Services under Grant Nos. CA-0848, CA-21445 and CA-21965.

Accordingly, the U.S. Government has certain rights in this invention.

This application is a continuation of Ser. No. 467,999, filed Feb. 18, 1983 now abandoned.

INTRODUCTION

This invention relates to typing human cells with monoclonal antibodies specific for an H antigen of O type cells. The monoclonal antibodies recognize the difucosyl-type 2-H antigen on human cells and are useful in assays for this antigen.

Blood must be typed to ensure compatibility between donor and recipient before a transfusion can be started. For purpose of typing, human blood is divided into the major groups A, B, AB and O. The surface structures of the cell membrane of the red blood cell determine the particular group to which the blood belongs. Typing into groups is made possible by reagents which recognize these specific cell surface determinants. In the case of the A and B determinants, antibodies to A and B surface antigens are used in immunological assays. In the case of O blood type, it is the H cell surface antigen which must be recognized. However, an H antibody has not been available for immunossay of O blood so O blood is currently typed with extracts of seed of *Ulex europeus* (common gorse) which acts somewhat like an anti-H antibody. (Boyd, W. C. et al, *Blood* 9:1195–1198 (1954)). This reagent lacks specificity for fine structures of the H antigen which may be of significance in some blood disorders. Moreover, quantitation of the H antigen is not possible with this reagent.

New possibilities for the detection of antigens arose with the development of the hybridoma technique for the production of monoclonal antibodies. (Kohler, G. and Milstein, C. *Nature* 256:495–497 (1975).) Although most monoclonal antibodies are developed for the purpose of detecting tumor-specific or tumor-associated antigens, in actual practice many of the hybridoma clones developed will produce antibodies for more common antigens as well. These antibodies are valuable tools for characterizing the cell surface in general or as diagnostic reagents.

Accordingly, a search was undertaken for a monoclonal antibody which would recognize the H antigen of the O blood group.

SUMMARY OF THE INVENTION

It was rather unexpectedly discovered that a monoclonal antibody produced from a human lung cancer cell line had specificity for the H antigenic determinant of the O blood type. This monoclonal antibody is a significant improvement in blood typing reagents and has diagnostic applications where the H antigenic determinant is of significance.

It was further observed that this monoclonal antibody had specificity for only one type of H antigenic determinant—the difucosyl-type 2-H determinant. By means of the monoclonal antibody it was possible to characterize the fine structure of this H determinant.

The monoclonal antibodies may be tagged and immobilized for use in quantitative in vitro assays of the difucosyl-type 2-H antigen. The antibodies are therefore of significant value in blood typing and in the diagnosis of blood disorders and other abnormalities associated with changes in the amount of this H antigen.

Accordingly, it is a principal object of the present invention to provide monoclonal antibodies which recognize the H antigen on human cells of the O penotype.

It is another principal object of the present invention to provide a method of typing human blood by means of monoclonal antibodies which recognize the H antigen of the O blood group.

It is a specific object of the present invention to provide antibodies which recognize the difucosyl-type 2-H antigen on human cells.

It is a further object of the present invention to provide a method of producing monoclonal antibodies which recognize the difucosyl-type 2-H antigen.

It is a further object of the present invention to provide a method for detecting difucosyl-type 2-H antigenic determinants in serum or other body fluids.

It is another object of the present invention to provide immunoassays for quantitatively measuring the amount of difucosyl-type 2-H antigenic determinant.

It is a further object of the present invention to provide a diagnostic method whereby malignant cells may be distinguished from non-malignant cells in humans who normally carry the difucosyl-type 2-H determinant.

In accordance with the present invention, monoclonal antibodies recognizing the H antigen, specifically the difucosyl-type 2-H antigen of human cells were prepared. They were prepared by the hybridoma technique wherein spleen cells from mice immunized with a human lung cancer line were fused with mouse myeloma cells. One of the hybrid clones produced a monoclonal IgM antibody (designated Deposit Number F-3) which was completely absorbed by O red cells and completely inhibited by low concentrations of H antigenic glycoproteins and hog mucin (A+H). Bombay red cells which lack the H antigen failed to absorb F-3 activity. Monoclonal antibody F-3 is, therefore, highly specific for O blood group determinants.

Binding assays with F-3 and a series of glycolipids isolated from the O-type red cell membrane showed that the determinant important for specificity of the F-3 antibody is of the difucosyl-type 2-H antigenic structure.

The monoclonal antibodies are useful in diagnostic assays for H antigen based on difucosyl-type 2-H determinant. Thus the antibodies are useful for typing blood, a reaction commonly performed on a large scale in blood banks. The monoclonal antibodies are also useful in the detection of serum markers, the H antigen, which may vary with disease. When the antibodies are bound to chromophoric groups, flourescent groups or a radioactive element, they may be used in standard binding assays, serological assays, such as, for example, the anti-mouse immunoglobulin M-MHA assays. Radioimmunoassay or enzyme-linked immunoassay wherein the antibodies are optionally immobilized on an inert support may be used for quantitative measurement of the amount of difucosyl-type 2-H antigen. The antibodies are of diagnostic value in cases where malignant cells lose or gain, in the process of differentiation, the H antigenic determinant normally found in cells in other healthy tissue such as blood. The antibodies are also of use in hematology research, especially where fine differences between structures of the H antigen are significant.

DETAILED DESCRIPTION OF THE INVENTION

The following description is intended to illustrate this inventron without limiting same in any manner especially with respect to substantially functional equivalents of hybridomas, monoclonal antibodies and cell lines described and claimed herein.

I. The Monoclonal Antibody Recognizing the H antigenic determinant of O cells

A. Synthesis

Materials

Human lung cancer cell lines were developed by procedures used previously in our laboratory (Dippold, W.; Lloyd, K. O; Li, L. T. C.; Ikeda, H.; Oettgen, H. F. and Old, L. J. *Proc. Natl. Acad. Sci. U.S.A.* 77:6114–6118 (1980)) from lung adenocarcinomas (SK-LC-2, -3 and -12), a lung squamous cell carcinoma (SK-LC-8) and a lung anaplastic carcinoma (SK-LC-6). $A_1$, $A_2$, $A_1B$, $A_2B$, O and B red cells were obtained from healthy laboratory personnel. Bombay ($O_h$) red cells from two different persons were kindly donated by W. L. Marsh from the New York Blood Center. Human ovarian cyst and hog gastric mucin blood group glycoproteins have been described (Lloyd, K. O. and Kabat, E. A., *Proc. Natl. Acad. Sci. U.S.A.* 61:1470–1477 (1968)). Ovarian cyst glycoproteins with high $Le^b$ (preparation 116) and low $Le^b$ (preparation 500) expression were gifts of Dr. W. M. Watkins, Clinical Research Center, Harrow, England. Blood group precursor glycoprotein (OG) (Vicari, G. and Kabat, G. A., *J. Immunol.* 102:821–825 (1969)) and horse B glycoprotein (Baer, H. et al., *J. Expt. Med.* 91:105–114 (1950)) were provided by Dr. E. A. Kabat, Columbia University, New York. Pneumococcal type XIV polysaccharide was a gift from Dr. M. Heidelberger, New York University Medical School, New York. Dr. K. Furukawa (Gunma University, Japan) donated the gastric cancer polysaccharide (GC6406.1). Blood group glycoproteins from saliva were obtained from Ortho Diagnostics. Smith degradation (a procedure which destroys A, B and O specificities and exposes precursor-type structures) was performed as described previously (Lloyd, K. O. and Kabat, G. A., supra).

Availability of cell lines, hybridomas and monoclonal antibodies

The cell lines, hybridomas and monoclonal antibodies disclosed in the present invention are deposited with Sloan-Kettering Institute, 1275 York Avenue, New York, N.Y. 10021. A preferred embodiment of the invention is designated F-3. This embodiment has been deposited with the American Type Culture Collection, 12301 Parklawn Drive, Rockville, Md., 20852, and bears ATCC designation HB8217. Deposit is for the purpose of enabling disclosure only and is not intended to limit the concept of the present invention to the particular materials deposited.

Immunization and cell fusion techniques (BALB/c×C57B16)$F_1$ female mice were immunized by four intraperitoneal injections of $2\times10^6$ SK-LC-3 cells over a 4 month period. A final immunization was given 3 days before the spleen cells were harvested for fusion.

Cell fusion was done as described (Dippold, W. et al., supra). Briefly, cells from mouse myeloma line MOPC-2 NS-1 were mixed with spleen cells from an immunized mouse and fused by adding 42% (wt/vol) polyethylene glycol in phosphate buffered saline with 15% (vol/vol) dimethylsulfoxide $1\times10^5$ cells in 1 ml HAT-medium were seeded in each well of 10 24-well Costar plates with attached human fetal lung fibroblast feeder layers. HAT-medium consisted of RPMI-1640 medium supplemented with 0.2 mM hypoxanthine, 80 $\mu$M aminopterin and 32 M thymidine.

Selection and cloning of hybridomas and passage in mice

Supernatants from growing cell colonies were harvested after 21 days and assayed for antibody activity using the anti-mouse Ig-MHA test. The screening panel consisted of 10 human cell lines [5 lung cancer lines: SK-LC-2, -3, -6, -8, -12; 3 other cancer lines: SK-RC-7 (kidney cancer), SK-MEL-37 (melanoma) and ME-180 (cervix cancer)]. Cells from antibody-producing colonies were subcloned (5 cells per well) 3 times in 96 well plates (Costar). Cultures of subcloned hybridomas were also injected subcutaneously into nude mice (Swiss background). Sera from mice with growing tumors were collected and stored at −20 C.

Determination of Ig-class

The globulin-fraction of F-3 hybridoma supernatant was concentrated 10 fold by salt precipitation. An Ouchterlony immunoprecipitation was carried out on immunodiffusion plates using subclass specific rabbit anti-mouse Ig.

B. Screening Tests

Serological assays

Mouse antibodies were detected with an anti-mouse Ig-MHA assay as described (Dippold, W. et al., supra) and with a hemagglutination assay. Indicator cells for the anti-mouse Ig - MHA were prepared by conjugating rabbit anti-mouse Ig (DAKO, Copenhagen) to human O red cells with 0.01% chromium chloride. Target cells were cultured in Terasaki microtest plates (Falcon) and incubated with hybridoma supernatants at 4° C. for 60 minutes. After washing with phosphate-buffered saline (PBS) with 5% gammaglobulin-free fetal bovine serum (FBS), to remove unbound antibody, a 0.2% suspension of indicator cells in phosphate-buffered saline with 5% gammaglobulin-free FBS was added for 45 minutes at room temperature. Red cell rosettes around target cells indicated bound antibody.

For the hemagglutination assay, doubling dilutions of the antibody were prepared in 96 well plates. An equal volume (25) of a 2% red cell suspension was added. The plates were incubated for 3 hours at room temperature and agglutination patterns were observed visually.

For absorption tests equal amounts of red cell pellets and F-3 antibody in appropriate dilutions were incubated for 60 minutes at 4° C. Absorbed supernatants were collected after centrifugation and tested with the anti-mouse Ig MHA assay for remaining antibody activity.

Inhibition tests were performed by diluting the test substance in phosphate-buffered saline in Terasaki microtest plates, adding equal amounts (10) of the approporiately diluted antibody and incubating the mixture for 60 minutes at 4° C. The mixture was then tested for remaining antibody activity against SK-LC-3 using the anti-mouse Ig-MHA test or by red cell agglutination.

C. Characterization of monoclonal antibody

Detection of F-3 monoclonal antibody activity

Hybridoma cell colonies were found in 43 out of 240 seeded wells. Nine of the 43 supernatants contained only very weak antibody reactivities, but one (F-3) showed a strong reactivity against some cells of the screening panel. This hybridoma supernatant reacted with all five lung cancer lines tested (SK-LC-2, -3, -6, -8 and -12), with a renal cancer cell line (SK-RC-7), and with a cervical carcinoma cell line (ME-180). It did not react with melanoma cell line SK-MEL-37. F-3 hybridoma clone (Deposit number Hybridoma F-3) was subcloned 4 times and grown in the nude mouse; it was shown to be producing IgM antibody $F_3$ (Deposit number Antibody F-3).

Reactivity of F-3 antibody with red cells

Lung cancer (SK-LC-2, -3, 06, -8 and -12) as well as renal cancer (SK-RC-7) and cervical cancer (ME-180) cell lines express ABO blood group antigens whereas melanoma cell lines (e.g. SK-MEL-37) do not. For this reason we tested monoclonal antibody F-3 for anti-blood group activity. Four samples of O red cells were able to absorb F-3 antibody completely whereas A and B cells were only partially effective and Bombay ($O_h$) cells were completely ineffective. A more detailed study of the reactivity of F-3 antibody with red cells of various blood types were carried out by quantitative absorption tests using F-3 in the form of nude mouse serum. Small numbers of O red cells completely absorbed F-3 antibody whereas red cells of other blood group types only partially absorbed antibody at the cell numbers tested. $A_2$ cells absorbed more antibody than $A_2B$ and B cells which in turn were more effective than $A_1$ cells. These results indicate that F-3 antibody is directed against H(O) blood group antigen which is known to be partially expressed on $A_2$ cells and to be completely absent from Bombay cells.

Direct agglutination tests of F-3 antibody with various red cells were completely consistent with the absorption assays. F-3 supernatants agglutinated O red cells at a titer of 1:128. Against $A_2$ red cells the titer was 1:32 and against B red cells 1:2. F-3 failed to agglutinate Bombay ($O_h$), $A_1$, $A_1B$ and $A_2B$ red cells (Table I). F-3 from nude mouse serum was a much stronger reagent. It agglutinated O red cells at a titer of 1:40,000, $A_2$ red cells at a titer of 1:640 and B cells at a titer of 1:80 (Table I).

TABLE I

Hemagglutination titers of F-3 antibody with different human red cells

| Red cell type | F-3 Source | |
|---|---|---|
| | Hybridoma Supernatant Titer | Nude mouse serum Titer |
| 0 (Lewis b+) | 1:128 | 1:40,000 |
| 0 (Lewis b−) | n.d. | 1:40,000 |
| $A_2$ | 1:32 | 1:640 |
| B | 1:2 | 1:80 |
| $A_1B$ | 0 | 1:20 |
| $A_1$ | 0 | 1:20 |

TABLE I-continued

Hemagglutination titers of F-3 antibody with different human red cells

| Red cell type | F-3 Source | |
|---|---|---|
| | Hybridoma Supernatant Titer | Nude mouse serum Titer |
| $O_h$ | 0 | n.d. |

The mouse monoclonal antibody F-3 of the present invention has the characteristics of an anti-H antibody. The hybridoma supernatant agglutinates normal O red cells at a titer of 1:128, and $A_2$ at 1:32. $A_1$, $A_1B$, $A_2B$ cells and Bombay ($O_h$) cells were not agglutinated by F-3. After passage of the clone in the nude mouse the titer of the mouse serum against O was 1:40,000, and 1:640 and 1:80 against $A_2$ and B cells, respectively. Different human red cells absorbed F-3 activity corresponding to their H-antigen content. F-3 was completely absorbed by normal O red cells, $A_2$ cells were more efficient than $A_1$ and B red cells and $O_h$ red cells did not absorb at all.

D. Inhibition of F-3 by soluble glycoproteins, polysaccharides and monosaccharides

TABLE II

| Substance tested | Minimum amount for complete inhibition (ug/ml) | |
|---|---|---|
| | Ig-MHA assay[1] | Hemagglutination assay[2] |
| H saliva glycoprotein | 0.5 | n.d.[3] |
| H ovarian cyst glycoprotein (Tighe) | 2 | 1.0 |
| H $Le^{b+}$ ovarian cyst glycoprotein (116) | n.d. | 2.0 |
| H $Le^{b-}$ ovarian cyst glycoprotein (500) | n.d. | 2.0 |
| Gastric cancer polysaccharide (GC 6406.1) | 23 | 3.6 |
| A + H hog mucin | 25 | 4.0 |
| B ovarian cyst glycoprotein (Beach) | 110 | 31 |
| A ovarian cyst glycoprotein (Sullivan) | 120 | 62 |
| $Le^a$ ovarian cyst glycoprotein (N-1) | 950 | 760 |
| H hog mucin (66) | 880 | 880 |
| Pneumococcus XIV polysaccharide | 1000 | 1000 |
| Inactive ovarian cyst glycoprotein (OG 10%) | 500 | 60 |
| B horse stomach glycoprotein (4) | 600 | 300 |
| A hog mucin (67) | 870 | 300 |
| Smith-degraded hog mucin | 1020 | 1020 |
| Dextran NRRL | 920 | n.d. |

[1]F-3 antibody (hybridoma supernantant 1:1000) tested against SK-LC-6 target cells using Ig-MHA assay
[2]F-3 antibody (nu/nu serum 1:4000) tested by agglutination of O red cells.
[3]n.d. - not determined.

Table II shows the ability of various substances to inhibit F-3 antibody as detected by the anti-mouse-Ig MHA test on SK-LC-6 target cells and by agglutination of O red cells. Results obtained with the two assay methods were generally in agreement although some variability was noted. Purified preparations of human H(O)-glycoproteins, hog gastric mucin (A+H), a gastric cancer polysaccharide and saliva from an O secretor inhibited F-3 at very low concentrations. Human A- and B-glycoproteins inhibited at higher concentrations. Other glycoproteins were weakly inhibitors or non-inhibitory at the highest concentration tested. H(O) glycoproteins from saliva and ovarian mucin inhibited F-3 at very low concentrations (Table II). Higher concentrations of purified glycoproteins from A- and B-secretors, which contain fewer H antigen determinants, were necessary to inhibit F-3. Hog mucin (A+H) and a gastric cancer polysaccharide preparation which contains large amounts of H antigen ((Vicari, G. et al., supra), also inhibited F-3 at low concentrations. OG glycoprotein and Smith-degraded A+H mucin were relatively non-inhibitory; this is consistent with the inability of F-3 to agglutinate Bombay cells as both these antigens lack ABH determinants and express precursor blood group or Ii specificities (Feizi, T., *J. Exp. Med.*, 133:37–52 (1971)). It is interesting that the human H, A and B glycoproteins are better inhibitors than the corresponding hog or horse preparations (Table II). Since F-3 is equally reactive with the Lewis b positive or negative red cell and glycoproteins it is unlikely that this difference is due to preferential reactivity of F-3 with Le$^b$ determinants. Whatever the explanation, the results indicate that F-3 has a specificity for fine differences in H structures.

E. Effect of neuraminidase treatment of Bombay ($O_h$) and O red cells

A red cell suspension (2%) in phosphate-buffered saline was mixed with an equal volume of *Vibrio cholerae* neuraminidase (500 U/ml, Behringwerke) and incubated for 15, 30 or 60 minutes at 37° C. The red cells were then washed twice with PBS and pelleted for absorption tests.

Neuraminidase-treated O and Bombay ($O_h$) red cells were incubated with F-3 to determine if H antigen expression could be generated. Enzyme-treated O red cells still absorbed F-3 completely whereas Bombay ($O_h$) red cells remained completely ineffective even after neuraminidase treatment. No change was observed in the agglutination titer of F-3 against enzyme-treated red cells.

Dodd and Lincoln observed a significant increase in the titer of Ulex anti-H with Bombay ($O_h$) red cells after treatment of the cells with neuraminidase (Dodd, B. and Lincoln, P. S., Vox Sang 35:168–175 (1978)). We treated normal O red cells and Bombay ($O_h$) cells with neuraminidase but no change in the ability of O or $O_h$ red cells to absorb F-3 activity, or in agglutination titers of F-3 against enzyme treated O and Bombay ($O_h$) red cells was found. We conclude that neuraminidase treatment failed to induce the expression of H antigen on Bombay ($O_h$) red cells as recognized by F-3 monoclonal antibody.

II. The difucosyl-type 2-H antigenic determinant

Nature of cell surface antigen

Blood group A, B, H(O) and Lewis antigens are inherited independently but are phenotypically related because of their biosynthetic interdependence. The antigenic determinants responsible for A, B, H and Lewis antigenicity on red cells and in secretions have been determined (Watkins, W. M. *Proc. Royal Soc. London B*, 202:31–53 Kabat, E. A. *Carbohydrates In Solution* (Ed. H. S. Isbell). Advances In Chemistry, Series 117, 334–361. American Chemical Society, Washington, D.C. (1973); Lloyd, K. O. Int. Rev. Sci. Organic Chemistry, Series 2, Volume 7 (GO Aspinall, Ed.), Butterworths, London (1976), p. 251–281.; Hakomori, S. *Seminars in Hematology* 18:39–62 (1981)). Following the proposals of Ceppellini (Ceppellini, R., In Ciba Found. Symp. on Biochemistry of Human Genetics p. 242–261, Churchill, London (1959)) and Morgan and Watkins (Watkins, W. M. and Morgan, W. T. J., Vox Sang. 4:97–119 (1959)), the biochemical basis for the expression of the various gene products and their inheritance has been explained in terms of the appropriate glycosyl transferases (Ginsburg, V., *Adv. Enzymology* 36:131–149 (1972)). Thus the H gene codes for a-α-L-fucosyl-transferase which adds L-fucose to a precursor structure. Individually completely lacking a functional H gene (i.e. homozygous for the silent gene, h) lack the fucosyl transferase and cannot add L-fucose to their precursor chains. Persons of this genotype (h/h) are called Bombay ($O_h$) type (Blende, Y. M., et al., Lancet i:903–904 (1952)). Such individuals may have A and B enzymes appropriate to their AB genotype but as these enzymes cannot function their red cells and secretions lack A, B and H antigens (Race, C. and Watkins, W. M., PEBS Lett. 27:125–130 (1972)). The expression of ABO antigens on cells other than red cells has not been well studied but it is known that epithelial cells, in general, express ABO antigens appropriate to their blood type (Marcus, D. M., *New Eng. J. Med.* 280:994–1006 (1979)). In this context, it is appropriate to note that the full expression of A or B antigens may be blocked in malignant cells (Masamune, H., *Tohohu J. Exp. Med.* 68:81–91 (1958)). In agreement with this observation, SK-LC-3, the cell line used to immunize mice in this study, lacks A and B antigenic determinants even though the red cell blood group of the parent was AB.

Structure of the difucosyl-type 2-H antigen

Purified glycolipids isolated from human and animal sources were used to determine the precise specificity of antibody F-3. The structures of these antigens are as follows:

| Structure[1] | Blood group Specificity | Source |
|---|---|---|
| 1. βGal(1⟶4)βGlcNAc(1⟶3)βGal(1⟶4)Glc—Cer | | Human erythrocytes |
| 2. βGal(1⟶3)βGlcNAc(1⟶3)βGal(1⟶4)Glc—Cer | | Human meconium |
| 3. βGal(1⟶3)βGlcNAc(1⟶3)βGal(1⟶4)Glc—Cer<br>     2<br>     ↑<br>  αFuc 1 | H | Human meconium (H-5-1) |

-continued

| Structure[1] | Blood group Specificity | Source |
|---|---|---|
| 4. $\beta\text{Gal}(1\rightarrow 4)\beta\text{GlcNAc}(1\rightarrow 3)\beta\text{Gal}(1\rightarrow 4)\text{Glc}-\text{Cer}$<br>     $\overset{2}{\uparrow}$<br>    $\alpha\text{Fuc 1}$ | H | Human erythrocytes (H-5-2) |
| 5. $\beta\text{Gal}(1\rightarrow 4)\beta\text{GlcNAc}(1\rightarrow 3)\beta\text{Gal}(1\rightarrow 4)\text{Glc}-\text{Cer}$<br>              $\overset{3}{\uparrow}$<br>            $\alpha\text{Fuc 1}$ | X | Dog intestine |
| 6. $\beta\text{Gal}(1\rightarrow 3)\beta\text{GlcNAc}(1\rightarrow 3)\beta\text{Gal}(1\rightarrow 4)\text{Glc}-\text{Cer}$<br>              $\overset{4}{\uparrow}$<br>            $\alpha\text{Fuc 1}$ | Le$^a$ | Human intestine (Le$^a$-5) |
| 7. $\beta\text{Gal}(1\rightarrow 4)\beta\text{GlcNAc}(1\rightarrow 3)\beta\text{Gal}(1\rightarrow 4)\text{Glc}-\text{Cer}$<br>     $\overset{2}{\uparrow}$         $\overset{3}{\uparrow}$<br>    $\alpha\text{Fuc 1}$   $\alpha\text{Fuc 1}$ | Y | Dog intestine (Y-6) |
| 8. $\beta\text{Gal}(1\rightarrow 3)\beta\text{GlcNAc}(1\rightarrow 3)\beta\text{Gal}(1\rightarrow 4)\text{Glc}-\text{Cer}$<br>     $\overset{2}{\uparrow}$         $\overset{4}{\uparrow}$<br>    $\alpha\text{Fuc 1}$   $\alpha\text{Fuc 1}$ | Le$^b$ | Human intestine Le$^b$-6 |

[1]Gal: D-galatose; GlcNAc: N—acetyl-D-glucosamine, Glc: D-glucose; Fuc: L-fucose; Cer: ceramide. Gal(1–)GlcNAc: type 1 structures; Gal(1–4)GlcNAc: type 2 structures.

wherein gal is galactose, fuc is fucose, glc is glucose, N is nitrogen, Ac is acetate and Cer is ceramide. The numbers in the brackets refer to the positions of the carbon atoms in the sugar residues.

The terminal end of these chains is the determinant for specificity of the antibody. The monoclonal antibody of the present invention recognizes the difucosyl-type 2-H determinant, number 7 above.

Binding Assays With Monoclonal Antibody F-3

To detect the binding of the monoclonal antibody, a direct binding assay was performed. In this assay, a sample of each antigenic determinant (1-7 supra)was placed in the well of a sample plate. Monoclonal antibody (1:500) was added to each well. After rinsing, the wells were contacted with rabbit anti-mouse IgG (H+L) bound to alkaline phosphatase. Only difucosyl-type 2-H antigen bound the antibody as observed from color development with the enzyme.

Monoclonal antibody F-3 is thus able to discriminate the fine differences in H structures between the cell surface antigens.

Serum Antibodies to the Difucosyl-Type 2-H Antigen

The difucosyl-type 2-H antigenic determinant may be used to generate natural antibodies in an animal. Thus a host animal, rabbit or mouse, for example, may be immunized with the purified determinant along with an appropriate adjuvant to form natural antibodies which may be harvested by methods known in the art. These natural antibodies are also of diagnostic value.

III. Quantitative Immunoassays of the Difucosyl-type 2-H Antigen

The monoclonal antibodies may be conjugated with a flourescent group, an enzyme capable of developing color with appropriate reagents, or radioactive elements, preferably $I^{125}$. These antibodies may also be immobilized or an inert surface preferably ceramic beads or inert bibulous mat. The antibodies thus tagged and immobilized may be used in radioimmunassays (RIA) or enzyme-linked immunoassay (ELISA) to quantitatively measure the amount of difucosyl-type 2-H antigen in samples of red blood cells, serum or other tissues.

Quantitative assay of this antigen is of important diagnostic value in diseases characterized by changes in the H antigen. Thus it is an important serum marker. Quantitative assays are also important in locating malignant cells wherein the H antigen is lost during differentiation.

What is claimed is:

1. F-3 monoclonal antibodies recognizing difucosyl-type 2-H antigen of human cells.

2. Antibody-producing hybridoma cell line characterized by the production of the antibodies claimed in claim 1.

3. F-3antibody-producing hybridoma cell line formed by fusing a myeloma derived cell strain with splenocytes derived from mice or rats immunized with human lung adenocarcinoma cells.

4. A method of forming an F-3 antibody-producing hybridoma cell line by fusing a myeloma derived cell strain with splenocytes derived from mice or rats immunized with human lung adenocarcinoma cells.

5. Immunoassay to determine the presence of difucosyl type 2-H antigen comprising contacting a sample suspected of containing said antigen with a monoclonal antibody of claim 1 under conditions favoring formation of complexes between said antigen and said antibody and observing formation of said complexes.

6. Immunoassay of claim 5 comprising radioimmunoassay.

7. Immunoassay of claim 5 comprising enzyne-linked-immunoassay.

8. Immunoassay of claim 5 comprising serological assay.

9. Immunoassay of claim 8 comprising anti-mouse IgM-MHA assay.

10. Immunoassay of claim 5 wherein said monoclonal antibody is immobilized on an inert support.

11. Immunoassay of claim 5 wherein said sample comprises cells having type O phenotype.

12. Immunoassay of claim 5, wherein said immunoassay is used to type blood.

13. Immunoassay of claim 5, wherein said sample comprises body fluid.

14. Method for detecting the presence of malignant cells in an individual comprising performing an immunoassay of claim 5, wherein said sample is a sample of said individual's tissue, and comparing the results of said assay to the results of an immunoassay of said individual's normal red blood cells.

* * * * *